US012711849B2

(12) United States Patent
Minai

(10) Patent No.: US 12,711,849 B2
(45) Date of Patent: Aug. 18, 2026

(54) CONNECTION STATE DETERMINATION METHOD AND CONNECTION STATE DETERMINATION SYSTEM

(71) Applicant: TERUMO KABUSHIKI KAISHA, Tokyo (JP)

(72) Inventor: Kazuya Minai, Kai (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 18/937,931

(22) Filed: Nov. 5, 2024

(65) Prior Publication Data

US 2025/0061794 A1 Feb. 20, 2025

Related U.S. Application Data

(63) Continuation of application No. PCT/JP2023/028144, filed on Aug. 1, 2023.

(30) Foreign Application Priority Data

Aug. 24, 2022 (JP) ................................ 2022-133450

(51) Int. Cl.
*G08B 21/04* (2006.01)
*A61M 5/14* (2006.01)
*G16H 40/20* (2018.01)

(52) U.S. Cl.
CPC ....... *G08B 21/0453* (2013.01); *A61M 5/1413* (2013.01); *G16H 40/20* (2018.01); *A61M 2205/18* (2013.01); *A61M 2205/6072* (2013.01)

(58) Field of Classification Search
CPC . G08B 21/0453; G16H 40/20; A61M 5/1413; A61M 2205/18; A61M 2205/6072
(Continued)

(56) References Cited

U.S. PATENT DOCUMENTS 11,340,137 B2 * 5/2022 Leclerc .................. G02B 6/385
2015/0034713 A1 * 2/2015 Jones ....................... G06K 7/10 235/375
(Continued)

FOREIGN PATENT DOCUMENTS

CN 111755881 A 10/2020
DE 20 2016 000 611 U1 3/2016
(Continued)

OTHER PUBLICATIONS

International Search Report and Written Opinion of the International Searching Authority issued in the corresponding International Patent Application No. PCT/JP2023/028144, dated Oct. 3, 2023 with English language translations.
(Continued)

*Primary Examiner* — Naomi J Small
(74) *Attorney, Agent, or Firm* — FOLEY & LARDNER LLP

(57) ABSTRACT

Provided are a connection state determination method and a connection state determination system that enable provision of work assistance to a medical worker to reduce workloads and human mistakes. The connection state determination method is a connection state determination method for determining a connection state between a plurality of medical devices each including a connection portion having a unique identifier, the connection state determination method including: detecting the connection portions of the respective medical devices; determining whether the identifiers of the detected connection portions are in a predetermined state; and determining the connection state between the plurality of medical devices, in accordance with whether the identifiers are in the predetermined state.

12 Claims, 14 Drawing Sheets

(58) Field of Classification Search
USPC ........................................................ 340/573.1
See application file for complete search history.

(56) References Cited

U.S. PATENT DOCUMENTS

| | | | | |
|---|---|---|---|---|
| 2019/0326012 | A1* | 10/2019 | Witt | G16H 10/60 |
| 2021/0074417 | A1* | 3/2021 | Pierson | G06Q 10/20 |
| 2021/0157463 | A1* | 5/2021 | Gerder-Kallisch | G16H 40/60 |
| 2022/0321660 | A1* | 10/2022 | Arrizza | H04B 5/48 |
| 2023/0238125 | A1* | 7/2023 | Satish | G06K 19/06009<br>705/2 |

FOREIGN PATENT DOCUMENTS

| | | | |
|---|---|---|---|
| JP | H11-319075 | A | 11/1999 |
| JP | 2005-334280 | A | 12/2005 |
| JP | 2011-130652 | A | 6/2011 |
| WO | WO-2017/135107 | A1 | 8/2017 |

OTHER PUBLICATIONS

Written Opinion of the International Searching Authority issued in the corresponding International Patent Application No. PCT/JP2023/028144, dated Oct. 3, 2023 with English translation.
Extended European Search Report issued in EP Appl. No. 23857134.3 dated Oct. 22, 2025.

* cited by examiner 1
100 MANAGEMENT APPARATUS
110 ELECTRONIC MEDICAL RECORD
50 INFORMATION PROCESSING APPARATUS
51 CONTROL UNIT
52 COMMUNICATION UNIT
53 INTERFACE UNIT
54 IMAGE PROCESSING UNIT
55 MEMORY
56 STORAGE UNIT
60 COMPUTER PROGRAM
10 INPUT APPARATUS
20 OUTPUT APPARATUS LABEL ID : 0001
LABEL ID : 0051
LABEL ID : 0123
LABEL ID : 1018
INFUSION BAG ID : 0002
INFUSION SET ID : 0003
INFUSION BAG ID : 0055
PUMP ID : 0010
PUMP
INFUSION SET ID : 0058
INFUSION BAG ID : 0222
INFUSION SET ID : 0105
INFUSION BAG ID : 0036
INFUSION SET ID : 0089
PUMP
PUMP ID : 0981
3-GANG STOPCOCK MANIFOLD ID : 0004
INFUSION SET ID : 0003
INFUSION SET ID : 0058
EXTENSION ID : 0005
EXTENSION ID : 0005
INDWELLING NEEDLE ID : 0006
PATIENT
: TWO-DIMENSIONAL BARCODE

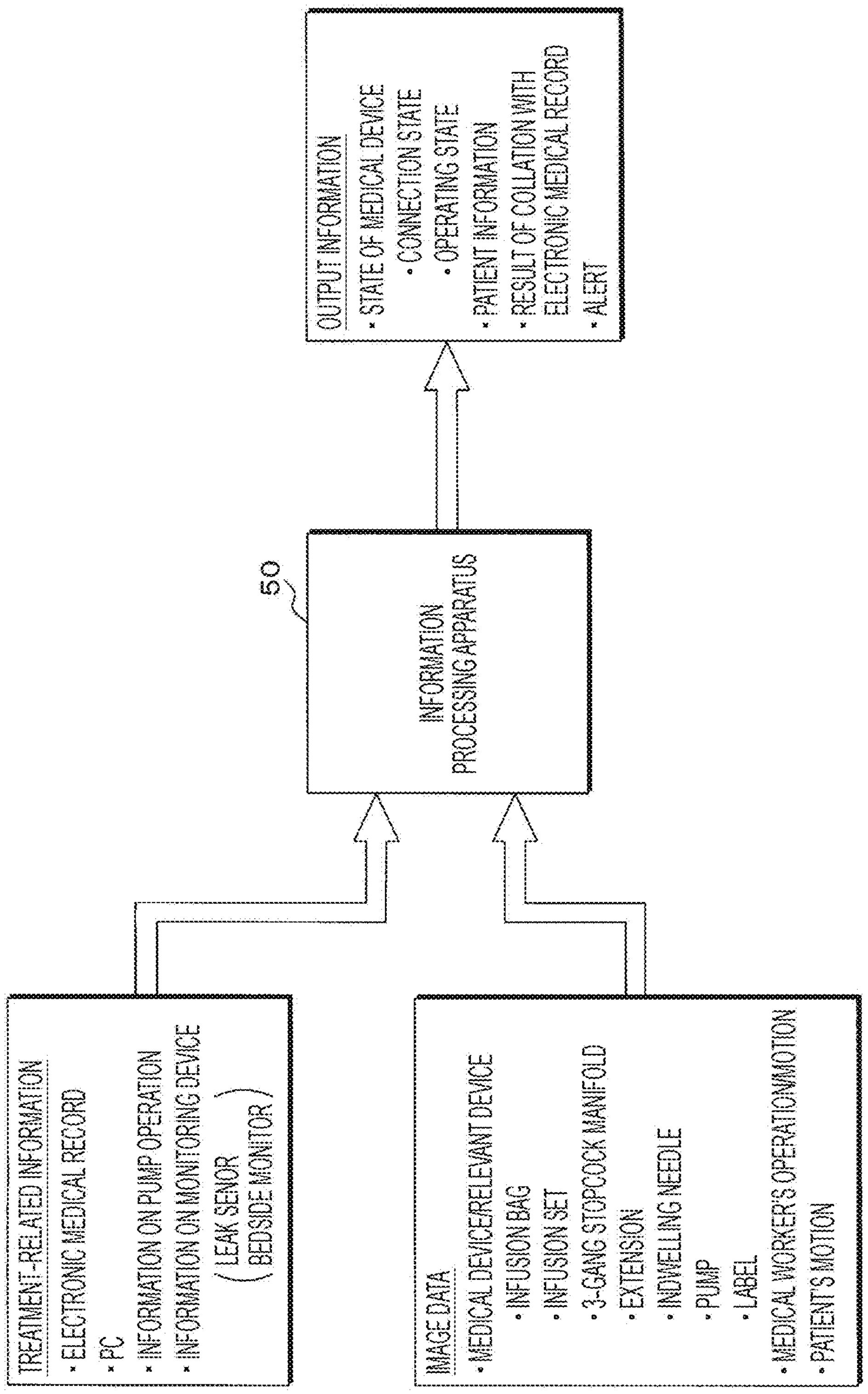

FIG. 3
TREATMENT-RELATED INFORMATION
· ELECTRONIC MEDICAL RECORD
· PC
· INFORMATION ON PUMP OPERATION
· INFORMATION ON MONITORING DEVICE
( LEAK SENOR
BEDSIDE MONITOR )
IMAGE DATA
· MEDICAL DEVICE/RELEVANT DEVICE
· INFUSION BAG
· INFUSION SET
· 3-GANG STOPCOCK MANIFOLD
· EXTENSION
· INDWELLING NEEDLE
· PUMP
· LABEL
· MEDICAL WORKER'S OPERATION/MOTION
· PATIENT'S MOTION
50
INFORMATION
PROCESSING APPARATUS
OUTPUT INFORMATION
· STATE OF MEDICAL DEVICE
· CONNECTION STATE
· OPERATING STATE
· PATIENT INFORMATION
· RESULT OF COLLATION WITH
ELECTRONIC MEDICAL RECORD
· ALERT

LABEL INFORMATION

LABEL IMAGE DATA, PATIENT ID, DRUG NAME

PUMP INFORMATION

FLOW RATE, SCHEDULED AMOUNT

PATIENT INFORMATION

PATIENT ID, NAME, AGE, SEX, ADMINISTERED DRUG NAME, ADMINISTRATION PERIOD, ADMINISTRATION AMOUNT, DISEASE NAME

10
PATIENT
INDWELLING NEEDLE ID:0006
EXTENSION ID:0005
3-GANG STOPCOCK MANIFOLD ID:0004
INFUSION SET ID:0003
PUMP
PUMP ID:0010
INFUSION SET ID:0003
INFUSION BAG ID:0002
LABEL ID:0001

FIG. 9

| CONNECTION PORTIONS | HISTORY INFORMATION | | | | |
|---|---|---|---|---|---|
| C1 | ○○:○○ ○○TH<br>CONNECTION CONFIRMATION | ΔΔ:○○ ○○TH<br>VISUAL INSPECTION CONFIRMATION | ΔΔ:XX ○XTH<br>ADDITIONAL TIGHTENING CONFIRMATION | ○○:ΔΔ ○XTH<br>CONNECTION CONFIRMATION | ... |
| C2 | ○○:○○ ○○TH<br>CONNECTION CONFIRMATION | ΔΔ:ΔΔ ○○TH<br>ADDITIONAL TIGHTENING CONFIRMATION | XX:ΔΔ ○XTH<br>VISUAL INSPECTION CONFIRMATION | ○○:XX ○ΔTH<br>VISUAL INSPECTION CONFIRMATION | ... |
| C3 | ○○:○○ ○○TH<br>CONNECTION CONFIRMATION | ○X:○○ ○ΔTH<br>ADDITIONAL TIGHTENING CONFIRMATION | XX:XX ΔΔTH<br>VISUAL INSPECTION CONFIRMATION | ○○:ΔΔ ○XTH<br>CONNECTION CONFIRMATION | ... |
| C4 | ○○:○○ ○○TH<br>CONNECTION CONFIRMATION | XX:XX ○XTH<br>VISUAL INSPECTION CONFIRMATION | XX:○○ ○XTH<br>VISUAL INSPECTION CONFIRMATION | ○○:Δ○ ○XTH<br>CONNECTION CONFIRMATION | ... |
| ... | ... | ... | ... | ... | ... |

CONNECTION STATE DETERMINATION METHOD AND CONNECTION STATE DETERMINATION SYSTEM

CROSS-REFERENCE TO RELATED APPLICATION

This application is a bypass continuation of PCT Application No. PCT/JP2023/028144, filed on Aug. 1, 2023, which claims priority to Japanese Patent Application No. 2022-133450, filed on Aug. 24, 2022. The entire contents of these applications are incorporated herein.

BACKGROUND

The present disclosure relates to a connection state determination method and a connection state determination system.

In medical settings, multiple medical devices and their relevant devices have occasionally been used for one patient. The number of medical devices to be used particularly in an operating room and an intensive care unit is larger than the number of medical devices to be used in a general ward. Japanese Patent Publication No. 2005-334280 A discloses, as an exemplary medical device, an infusion set including an infusion tube and connection portions disposed on two ends of the infusion tube.

SUMMARY

These medical devices directly affect the condition of patient's health in the event of trouble. For this reason, one of important tasks of medical workers is management and observation of the medical devices, and the medical workers currently spend time and effort on this task.

Embodiments of the present disclosure have been developed in view of the circumstances described above. An object of certain embodiments is to provide a connection state determination method and a connection state determination system that enable provision of work assistance to a medical worker to reduce workloads and human mistakes.

(1) A connection state determination method according to the present invention is a connection state determination method for determining a connection state between a plurality of medical devices each including a connection portion having a unique identifier, the connection state determination method including: detecting the connection portions of the respective medical devices; determining whether the identifiers of the detected connection portions are in a predetermined state; and determining the connection state between the plurality of medical devices, in accordance with whether the identifiers are in the predetermined state.

According to embodiments of the present invention, the following are provided.

(2) The connection state determination method recited above in (1) includes determining that the plurality of medical devices are connected, in a case in which the identifiers are in the predetermined state.

(3) In the connection state determination method recited above in (1) or (2), the predetermined state includes at least one of a state in which a separation distance between the identifiers of the respective connection portions is a predetermined distance or less and a state in which an arrangement of the identifiers of the respective connection portions is within a predetermined range.

(4) The connection state determination method recited above in any one of (1) to (3) includes recording a date and time of a determination that the plurality of medical devices are connected.

(5) The connection state determination method recited above in any one of (1) to (4) includes: determining whether a predetermined operation is performed on the connection portions by a medical worker; and recording a date and time of a determination that the predetermined operation is performed.

(6) The connection state determination method recited in (5) includes recording, in a case of determining that the predetermined operation is performed and then determining that the plurality of medical devices are connected, a date and time of a determination that the plurality of medical devices are connected.

(7) The connection state determination method recited above in any one of (1) to (6) includes outputting a warning in a case of determining that the plurality of medical devices are not connected or in a case in which a first predetermined period elapses from a date and time of a determination that the plurality of medical devices are connected.

(8) The connection state determination method recited above in any one of (1) to (7) includes outputting a warning in a case in which positions of the identifiers of the respective connection portions change or in a case in which a frequency of change in the positions is a predetermined threshold value or more.

(9) The connection state determination method recited above in any one of (1) to (8) includes outputting a warning in a case of determining that a predetermined operation is not performed on the connection portions within a second predetermined period from a date and time of a determination that the predetermined operation is performed on the connection portions.

(10) In the connection state determination method recited above in any one of (1) to (9), the identifiers each include a barcode.

(11) The connection state determination method recited above in any one of (1) to (10) includes: detecting the connection portions of the respective medical devices by capturing an image of the connection portions with an input apparatus; and determining whether the identifiers of the detected connection portions are in the predetermined state, based on the captured image.

(12) A connection state determination system according to the present invention is a connection state determination system for determining a connection state between a plurality of medical devices each including a connection portion having a unique identifier, the connection state determination system including: a detection unit that detects the connection portions of the respective medical devices; and a control unit configured to determine whether the identifiers of the detected connection portions are in a predetermined state, and a determine the connection state between the plurality of medical devices based on whether the identifiers are in the predetermined state.

Certain embodiments of the present disclosure enable provision of work assistance to a medical worker to reduce workloads and human mistakes.

BRIEF DESCRIPTION OF THE DRAWINGS

FIG. 3 is a diagram illustrating an outline of processing by an information processing apparatus.

FIG. 9 is a diagram illustrating exemplary history information.

DETAILED DESCRIPTION

Figure 1:
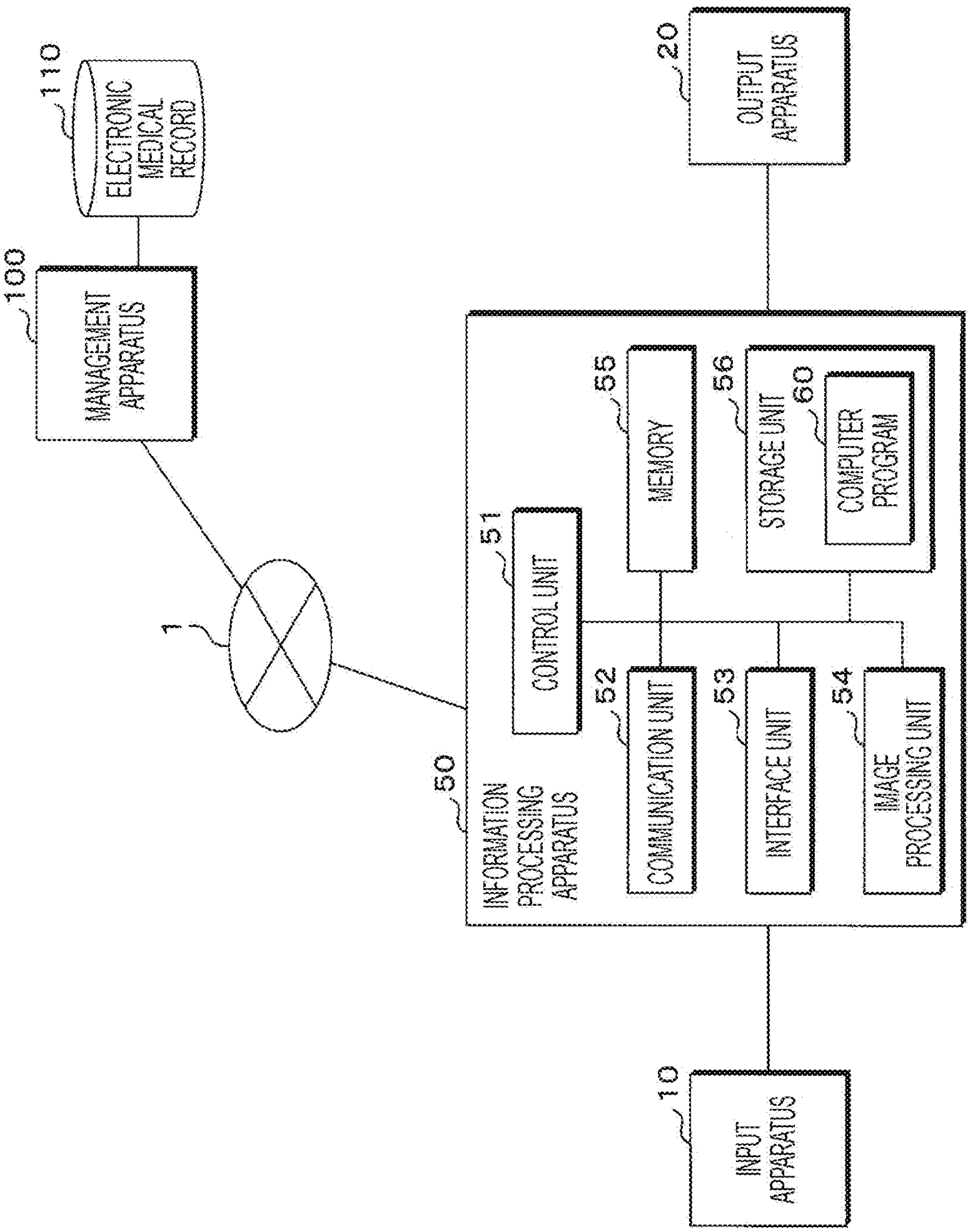
FIG. 1 is a diagram illustrating an exemplary configuration of a system for determining a connection state between medical devices according to the present embodiment.

An embodiment of the present invention will be described below. FIG. 1 is a diagram illustrating an exemplary configuration of a system for determining a connection state between medical devices according to the present embodiment. The system for determining a connection state between medical devices includes an input apparatus 10, an output apparatus 20, an information processing apparatus 50, and a management apparatus 100. The management apparatus 100 is accessible to an electronic medical record 110. It should be noted that the management apparatus 100 may be accessible to, instead of the electronic medical record 110, software associated with the electronic medical record 110, another specific software, or the like. The information processing apparatus 50 is connected to the management apparatus 100 via a communication network 1. Examples of the medical devices may include, but not limited to, an infusion bag, an infusion label, an infusion set, a pump, a 3-gang stopcock manifold (three-way stopcock manifold), a backflow prevention valve, an extension tube, an indwelling needle, a blood vessel access device, and the like.

The input apparatus 10 may be, for example, any one of a pair of augmented reality (AR) goggles, a smartphone, a tablet terminal, a camera, and the like. The input apparatus 10 is capable of capturing an image of a medical device and an image of connected connection portions of medical devices and outputting the captured images to the information processing apparatus 50. The connection portion of each medical device has a unique identifier; therefore, a captured image of the connection portion includes the identifier. The present embodiment exemplifies a two-dimensional barcode as an identifier; however, the identifier is not limited to a two-dimensional barcode as long as a connection portion can be identified with the identifier. The input apparatus 10 is also capable of capturing an image of medical worker's operation or motion and an image of patient's motion and outputting the captured images to the information processing apparatus 50. The input apparatus 10 may alternatively be a read apparatus, such as a barcode reader, for reading a two-dimensional barcode affixed to a medical device.

The management apparatus 100 is practicable using, for example, a server, a personal computer (PC), or the like. The management apparatus 100 includes a control unit that controls the entire management apparatus 100, a communication module, a hard disk or a semiconductor memory capable of recording required information, and the like. The management apparatus 100 records treatment-related information regarding each medical device with the treatment-related information correlated with the unique identifier of the medical device. Examples of the treatment-related information may include, but not limited to, information on pump operation (e.g., a flow rate, etc.), information on a monitoring device such as a leak sensor or a bedside monitor, information on a patient such as a patient's electronic medical record, information on a PC, and the like. The information processing apparatus 50 is capable of exchanging required information with the management apparatus 100.

The output apparatus 20 may be, for example, any one of a monitor, a pair of AR goggles, a smartphone, a tablet terminal, a PC, and the like. The output apparatus 20 is capable of displaying a result of processing by the information processing apparatus 50.

The information processing apparatus 50 includes a control unit 51 that controls the entire information processing apparatus 50, a communication unit 52, an interface unit 53, an image processing unit 54, a memory 55, and a storage unit 56. The storage unit 56 is practicable using, for example, a hard disk, a semiconductor memory, or the like. The storage unit 56 stores a computer program 60 (program product) and required information. The computer program 60 may be downloaded from an external apparatus via the communication unit 52 and stored in the storage unit 56. The computer program 60 may alternatively be recorded in a recording medium (e.g., an optically readable disk storage medium such as a CD-ROM), read by a recording medium read unit, and stored in the storage unit 56. The functions of the information processing apparatus 50 may be shared among a plurality of information processing apparatuses.

The control unit 51 includes a required number of central processing units (CPUs), micro-processing units (MPUs), graphics processing units (GPUS), and the like incorporated therein. The control unit 51 is capable of executing processing defined by the computer program 60. In other words, the processing by the control unit 51 refers to the processing based on the computer program 60.

The computer program 60 can be deployed so as to be executed on a single computer or a plurality of computers that are mutually connected via a communication network.

The communication unit 52 includes a communication module that is capable of exchanging required information with the management apparatus 100 via the communication network 1.

The memory 55 is practicable using a semiconductor memory such as a static random access memory (SRAM), a dynamic random access memory (DRAM), or a flash memory. The control unit 51 is capable of executing the computer program 60 deployed in the memory 55.

The interface unit 53 performs an interface function between the information processing apparatus 50 and the input apparatus 10 and between the information processing apparatus 50 and the output apparatus 20.

The image processing unit 54 determines whether two-dimensional barcodes affixed to connection portions of two medical devices are in a predetermined state, based on an image acquired from the input apparatus 10. The image processing unit 54 is also capable of determining medical worker's operation or motion and patient's motion, based on images acquired from the input apparatus 10.

Figure 2:
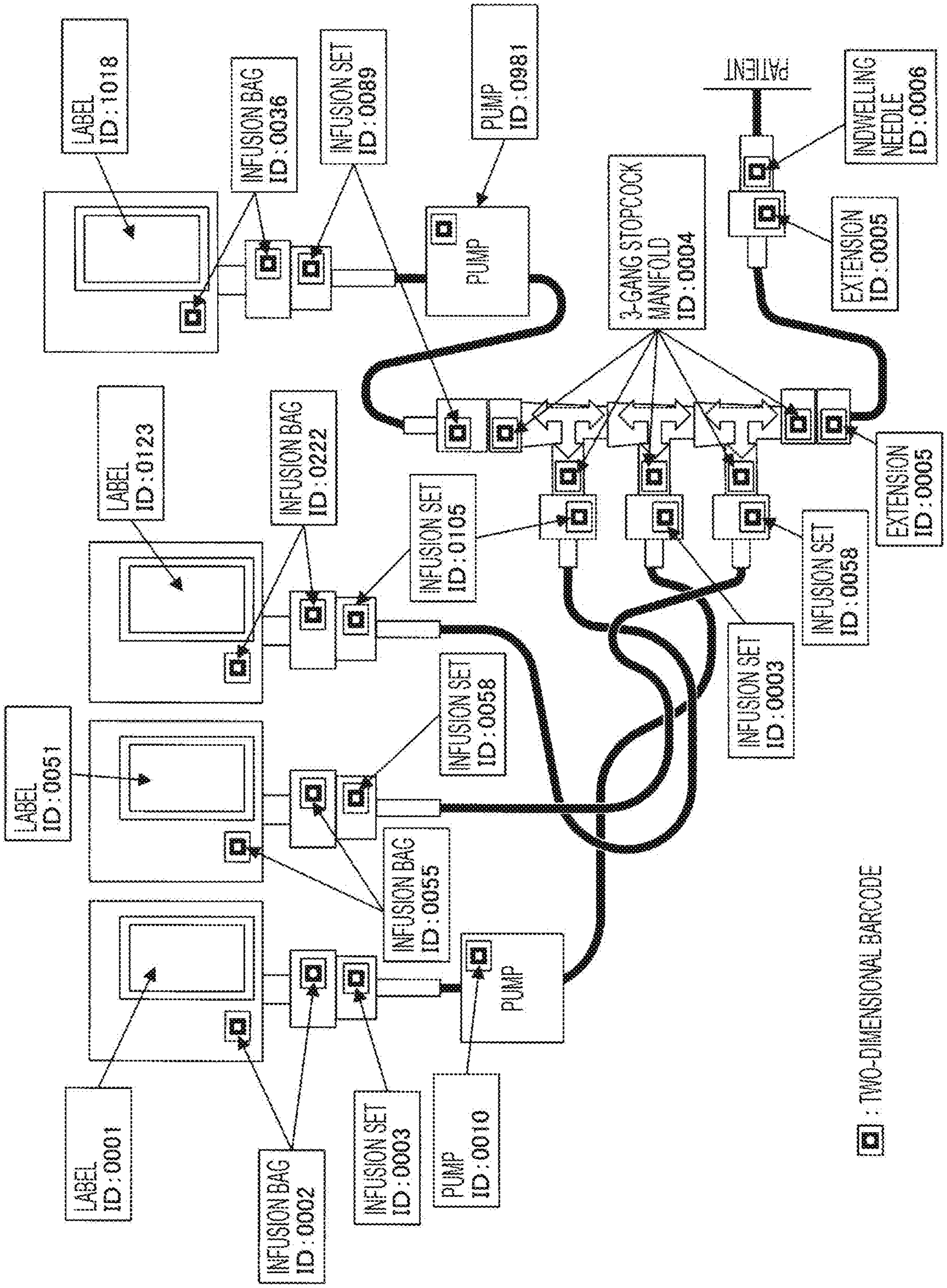
FIG. 2 is a diagram illustrating a plurality of exemplary medical devices to be used for one patient.

FIG. 2 is a diagram illustrating a plurality of exemplary medical devices to be used for one patient. As illustrated in FIG. 2, a plurality of medical devices are connected such that infusion fluids in four infusion bags can be administered to one patient. It should be noted that the connection state between the medical devices illustrated in FIG. 2 is merely exemplary and not restrictive. Although many more medical devices are used in actual medical settings, a connection state between medical devices is described herein using the example illustrated in FIG. 2 for convenience. Examples of the infusion fluids may include a drug solution, a corrective electrolyte solution, a physiological saline solution, and other fluids that can be administered to a living body. Examples of a drug in the drug solution may include, but not limited to, a sedative, an intravenous anesthetic, an anesthetic sedative, a local anesthetic, a nondepolarizing muscle relaxant, a pressor agent, an antihypertensive agent, a coronary vasodilator, a diuretic agent, an antiarrhythmic agent, a bronchodilator, a hemostatic agent, a vitamin compound, an antibiotic, a fat emulsion, and the like. The connection portion of each medical device has a two-dimensional barcode including an ID for identifying the connection portion.

As illustrated in FIG. 2, one connection portion (ID: 0003) of an infusion set is connected to a connection portion (ID: 0002) of an infusion bag to which a label (ID: 0001) is affixed. A pump (ID: 0010) is provided on the way to the infusion set. A first connection portion (ID: 0004) of a 3-gang stopcock manifold is connected to another connection portion (ID: 0003) of the infusion set. One connection portion (ID: 0005) of an extension tube (EXTENSION) is connected to a second connection portion (ID: 0004) of the 3-gang stopcock manifold. A connection portion (ID: 0006) of an indwelling needle is connected to another connection portion (ID: 0005) of the extension tube. The indwelling needle is indwelled in a patient's blood vessel.

One connection portion (ID: 0058) of an infusion set is connected to a connection portion (ID: 0055) of an infusion bag to which a label (ID: 0051) is affixed. A third connection portion (ID: 0004) of the 3-gang stopcock manifold is connected to another connection portion (ID: 0058) of the infusion set.

One connection portion (ID: 0105) of an infusion set is connected to a connection portion (ID: 0222) of an infusion bag to which a label (ID: 0123) is affixed. A fourth connection portion (ID: 0004) of the 3-gang stopcock manifold is connected to another connection portion (ID: 0105) of the infusion set.

One connection portion (ID: 0089) of an infusion set is connected to a connection portion (ID: 0036) of an infusion bag to which a label (ID: 1018) is affixed. A pump (ID: 0981) is provided on the way to the infusion set. A fifth connection portion (ID: 0004) of the 3-gang stopcock manifold is connected to another connection portion (ID: 0089) of the infusion set.

FIG. 3 is a diagram illustrating an outline of the processing by the information processing apparatus 50. The information processing apparatus 50 receives image data from the input apparatus 10, and also receives treatment-related information from the management apparatus 100. Examples of the image data may include image data on a captured image of a medical device (including its relevant device), image data on a captured image of connected connection portions of medical devices, image data on a captured image of medical worker's operation or motion, image data on a captured image of patient's motion, and the like. Examples of the medical devices may include, but not limited to, an infusion bag, an infusion set, a 3-gang stopcock manifold, an extension tube, an indwelling needle, a pump, a label, and the like. Examples of the treatment-related information may include, but not limited to, information on an electronic medical record, information on a PC, information on pump operation (operating status), information on a monitoring device such as a leak sensor or a bedside monitor, and the like.

Using the received image data and treatment-related information, the information processing apparatus 50 performs predetermined processing and outputs output information. The output information is output to the output apparatus 20 for the purposes of display and the like, and is also output to the management apparatus 100 for the purpose of recording. Examples of the output information may include, but not limited to, a state of a medical device (e.g., a connection state between connection portions of medical devices, an operating state of a medical device, etc.), patient information, a result of collation with an electronic medical record, a required alert, and the like.

Next, a specific example of the output information is described.

Figure 4:
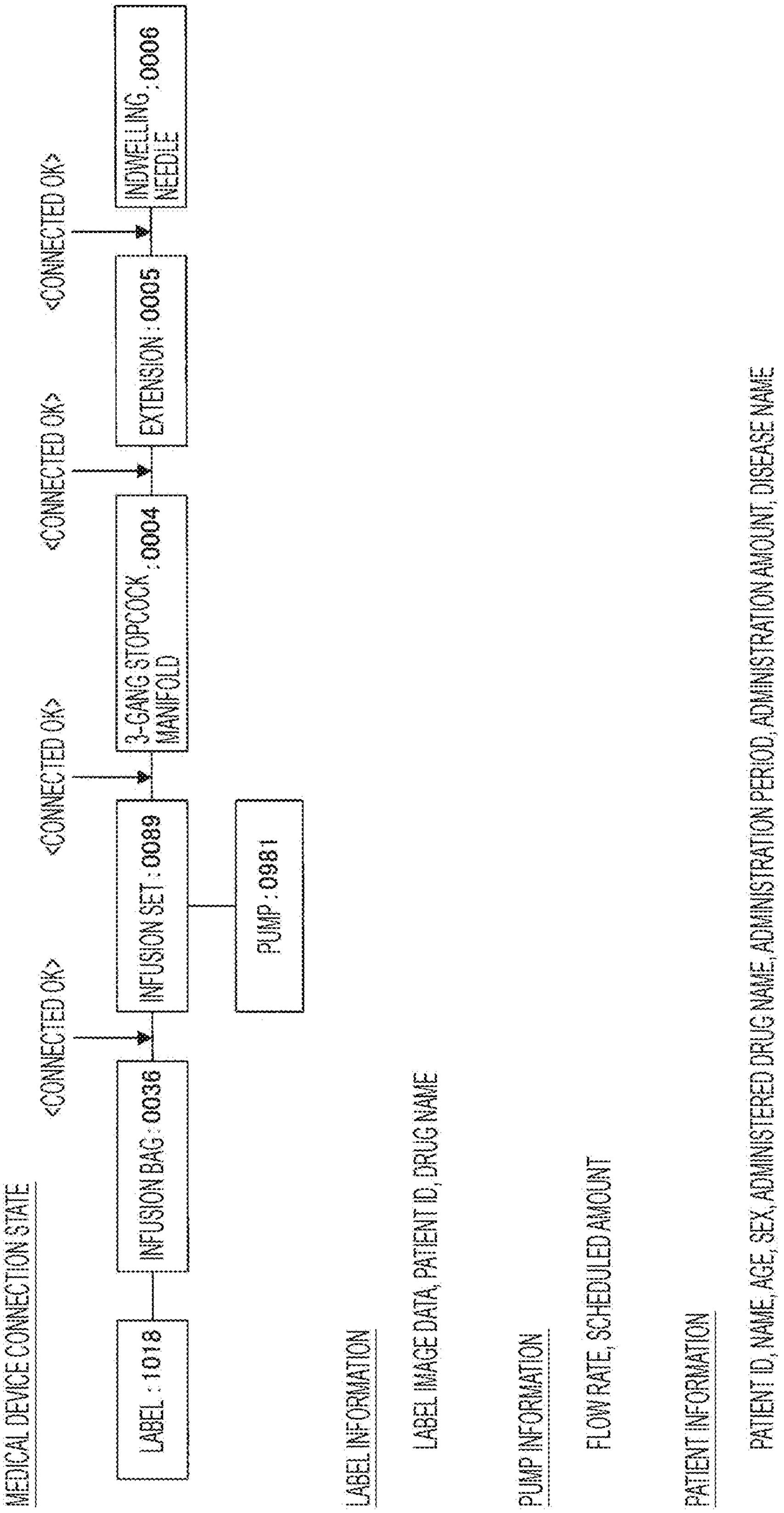
FIG. 4 is a diagram illustrating exemplary output information.

FIG. 4 is a diagram illustrating exemplary output information. The output information can be displayed on a display panel of a smartphone or a tablet terminal, a monitor of a personal computer or the like, a pair of AR glasses of a pair of AR goggles, or the like. First, a medical worker captures images of connection portions of a plurality of medical devices (see FIG. 2) placed in an operating room, an intensive care unit, or a sickroom, using a pair of AR goggles, a smartphone, a tablet terminal, or the like. The connection portions include, for example, a connection portion to which a two-dimensional barcode recording "infusion bag ID: 0002" is affixed, a connection portion to which a two-dimensional barcode recording "infusion set ID 0003" is affixed, and the like. In a case in which images of the connection portions of the plurality of medical devices can be captured with a camera placed in the operating room, the intensive care unit, or the sickroom, the camera may be used. An image capturing timing may be set in advance. The image capturing timing may alternatively be, for example, a timing when a new medical device is added or a timing when a medical worker changes.

FIG. 4 illustrates, as exemplary output information, a medical device connection state, label information, pump information, and patient information. First, the medical device connection state includes a connection status of a plurality of medical devices, and a connection state between connection portions of the medical devices (connected or not connected). FIG. 4 schematically illustrates an exemplary connection status of medical devices so as to allow a medical worker to easily confirm that "label: 1018," "infusion bag:

0036," "infusion set: 0089," "3-gang stopcock manifold: 0004," "extension tube: 0005," and "indwelling needle: 0006" are connected in this order and "pump: 0981" is connected to "infusion set: 0089." FIG. 4 also illustrates, as an exemplary connection state between connection portions of medical devices, a connection state between a connection portion of "infusion bag: 0036" and a connection portion of "infusion set: 0089," a connection state between a connection portion of "infusion set: 0089" and a connection portion of "3-gang stopcock manifold: 0004," a connection state between a connection portion of "3-gang stopcock manifold: 0004" and a connection portion of "extension tube: 0005," and a connection state between a connection portion of "extension tube: 0005" and a connection portion of "indwelling needle: 0006" (illustrated as <CONNECTED> in FIG. 4). A connection state determination method will be described later.

Label information can be acquired in such a manner that a medical worker captures an image of a label affixed to an infusion bag. Examples of the label information may include image data on a label, a patient ID (that may include a name and an age), a drug name, and the like. It should be noted that the label information may include the amount of a drug to be administered, the ingredients of a drug, and the like in accordance with the content of a label.

Pump information can be integrated by acquiring, from the management apparatus 100, medical-related information to be associated with a pump ID. Examples of the pump information may include a flow rate, a scheduled amount (administration amount), and the like set for a pump.

Patient information can be generated from, for example, a patient's electronic medical record acquirable from the management apparatus 100. Examples of the patient information may include, but not limited to, a patient ID, a name, an age, a sex, an administered drug name, an administration period, an administration amount, a disease name, and the like.

Next, a method of determining connection portions of medical devices is described.

Figure 5:
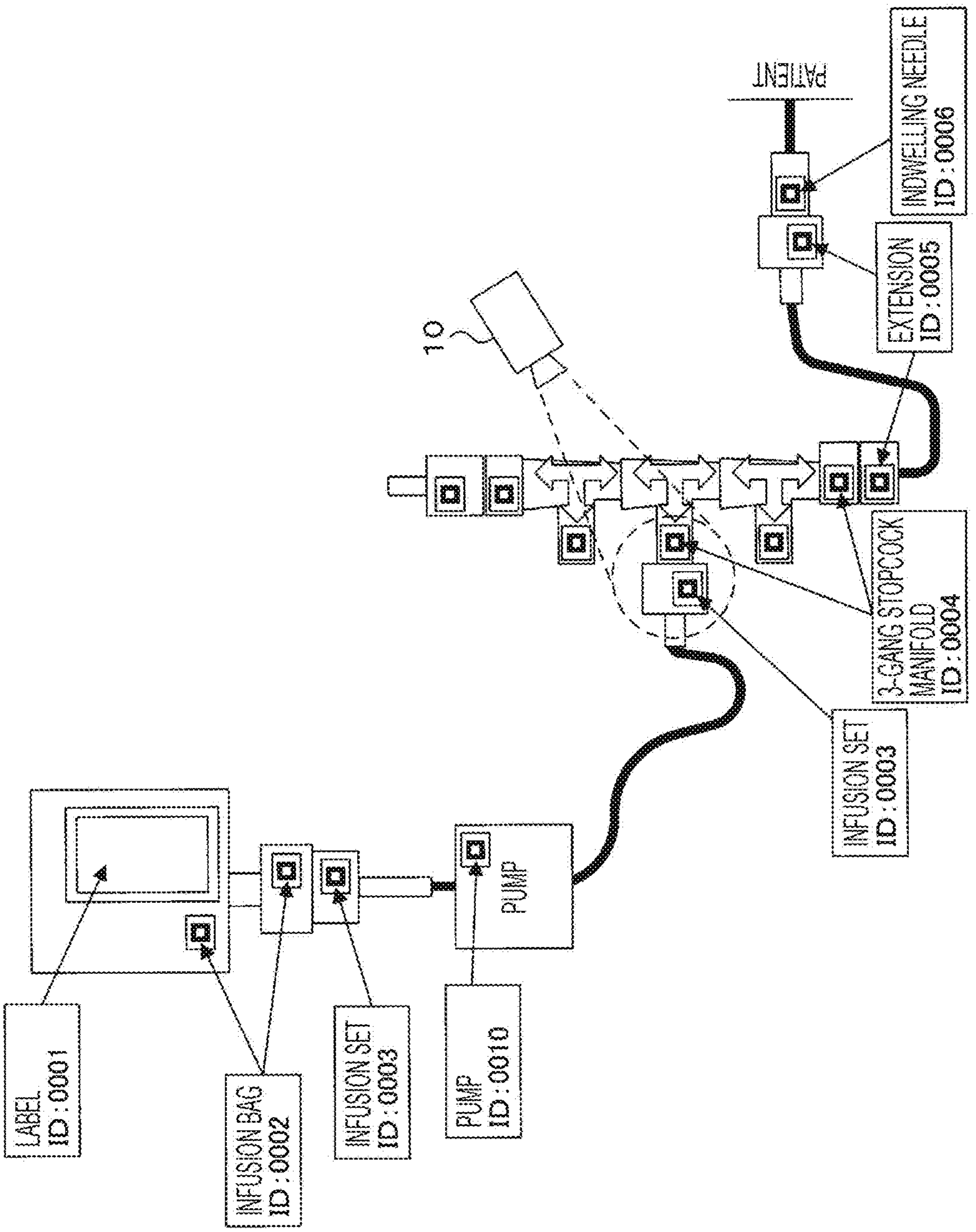
FIG. 5 is a diagram illustrating an exemplary connection status of a plurality of medical devices.

FIG. 5 is a diagram illustrating an exemplary connection status of a plurality of medical devices. For convenience, the medical devices illustrated in FIG. 5 correspond to some of the medical devices illustrated in FIG. 2. That is, one connection portion (ID: 0003) of an infusion set is connected to a connection portion (ID: 0002) of an infusion bag to which a label (ID: 0001) is affixed. A pump (ID: 0010) is provided on the way to the infusion set. A first connection portion (ID: 0004) of a 3-gang stopcock manifold is connected to another connection portion (ID: 0003) of the infusion set. One connection portion (ID: 0005) of an extension tube is connected to a second connection portion (ID: 0004) of the 3-gang stopcock manifold. A connection portion (ID: 0006) of an indwelling needle is connected to another connection portion (ID: 0005) of the extension tube. The indwelling needle is indwelled in a patient's blood vessel.

It is assumed that a medical worker captures an image of the connected connection portions of "infusion set: 0003" and "3-gang stopcock manifold: 0004," using the input apparatus 10 such as a smartphone, a tablet terminal, or a pair of AR goggles. Image data on the captured image is output to the information processing apparatus 50. The control unit 51 of the information processing apparatus 50 determines a connection state between the connection portion of "infusion set: 0003" and the connection portion of "3-gang stopcock manifold: 0004." The same applies to the remaining connection portions.

Figure 6A:
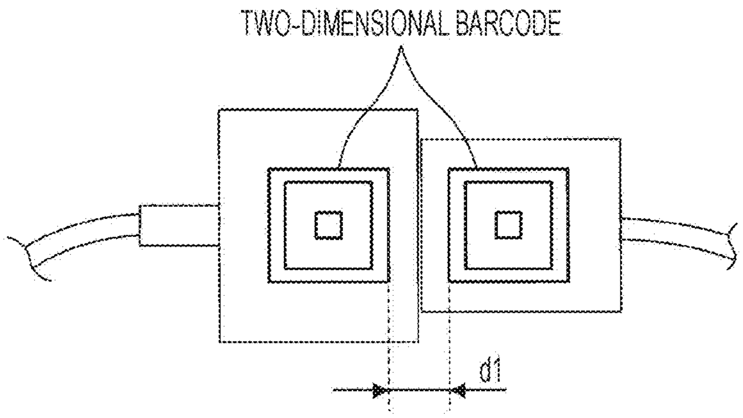
FIG. 6A is a diagram illustrating a first example of a method for determining a connection state between connection portions.
Figure 6B:
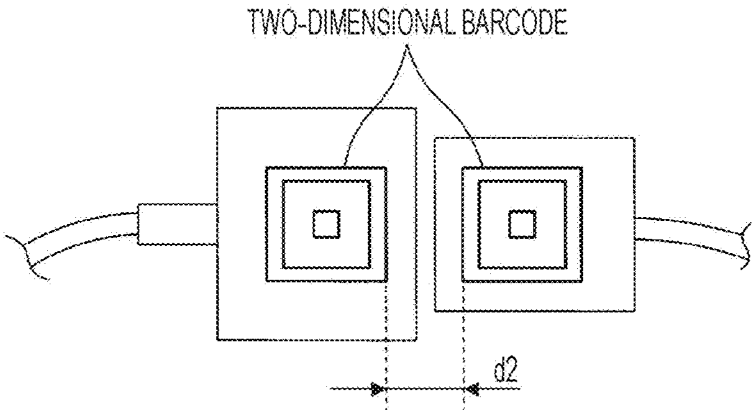
FIG. 6B is a diagram illustrating a first example of a method for determining a connection state between connection portions.

FIGS. 6A and 6B are diagrams each illustrating a first example of the method for determining the connection state between the connection portions. The image processing unit 54 determines whether the two-dimensional barcode affixed to the connection portion of "infusion set: 0003" and the two-dimensional barcode affixed to the connection portion of "3-gang stopcock manifold: 0004" are in a predetermined state. FIG. 6A illustrates a case in which the two-dimensional barcodes affixed to the respective connection portions are in the predetermined state. FIG. 6B illustrates a case in which the two-dimensional barcodes affixed to the respective connection portions are not in the predetermined state.

In the case illustrated in FIG. 6A, a separation distance d1 between edges of the two two-dimensional barcodes is a predetermined distance or less. In the case illustrated in FIG. 6B, a separation distance d2 (>d1) between the edges of the two two-dimensional barcodes is not the predetermined distance or less. That is, the predetermined state can be defined as the state in which the separation distance between the two-dimensional barcodes affixed to the respective connection portions is the predetermined distance or less.

The control unit 51 determines a connection state between the medical devices, in accordance with whether the two-dimensional barcodes affixed to the respective connection portions are in the predetermined state. Specifically, the control unit 51 can determine that the medical devices are connected, when the two-dimensional barcodes affixed to the respective connection portions are in the predetermined state. The control unit 51 can also determine that the medical devices are not connected, when the two-dimensional barcodes affixed to the respective connection portions are not in the predetermined state.

The first example of the determination method can facilitate, for example, a determination on a connection state between connection portions of such a type that connectors are attached to or detached from each other along their axes, a determination on a connection state between connection portions of such a type that a male connector is inserted into a female connector, and the like.

Figure 7A:
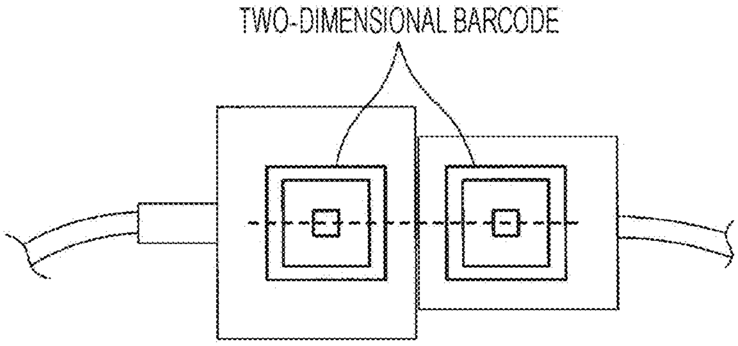
FIG. 7A is a diagram illustrating a second example of a method for determining a connection state between connection portions.
Figure 7B:
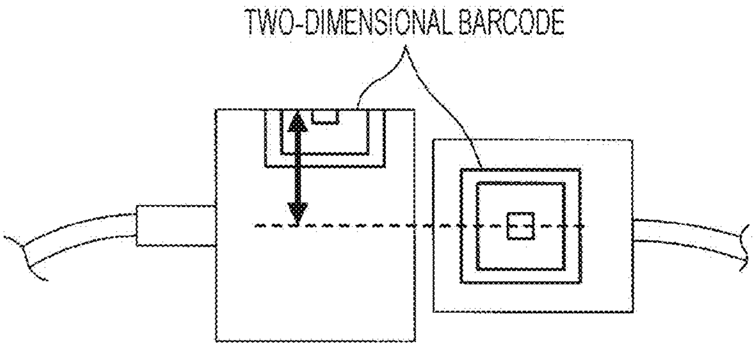
FIG. 7B is a diagram illustrating a second example of a method for determining a connection state between connection portions.

FIGS. 7A and 7B are diagrams each illustrating a second example of the method for determining the connection state between the connection portions. FIG. 7A illustrates a case in which the two-dimensional barcodes affixed to the respective connection portions are in the predetermined state. FIG. 7B illustrates a case in which the two-dimensional barcodes affixed to the respective connection portions are not in the predetermined state. In the case illustrated in FIG. 7A, an arrangement of the two two-dimensional barcodes is within a predetermined range. On the other hand, in the case illustrated in FIG. 7B, the arrangement of the two two-dimensional barcodes is not within the predetermined range. The predetermined range means that an angle of rotation about an axis connecting two connection portions (indicated by a broken line in FIGS. 7A and 7B) is within a predetermined angle of rotation (e.g., 45°, etc.). That is, the predetermined state can be defined as the state in which the arrangement of the two-dimensional barcodes affixed to the respective connection portions is within the predetermined range.

The control unit 51 determines a connection state between the medical devices, in accordance with whether the two-dimensional barcodes affixed to the respective connection portions are in the predetermined state. Specifically, the control unit 51 can determine that the medical devices are connected, when the two-dimensional barcodes affixed to the respective connection portions are in the predetermined state. The control unit 51 can also determine that the medical devices are not connected, when the two-dimensional barcodes affixed to the respective connection portions are not in the predetermined state.

The second example of the determination method can facilitate, for example, a determination on a connection state between connection portions of such a type that connectors are attached to or detached from each other by rotating the connectors about their axes. It should be noted that one of or both the first example of the determination method and the second example of the determination method may be used. Alternatively, a determination method may be selected in accordance with the type of a connection portion.

As described above, a connection state between connection portions of medical devices can be determined only by capturing an image of the connection portions (i.e., detecting the connection portions). It is therefore possible to easily confirm a situation in which although a medical worker connects medical devices to each other, the connection portions are disconnected from each other, and a situation in which a medical worker erroneously connects medical devices to each other. It is thus possible to provide work assistance to a medical worker and to reduce workloads and human mistakes.

Next, how to manage a plurality of medical devices is described. A medical worker is able to confirm states of a plurality of medical devices and states of connection portions of the medical devices and to record a result of the confirmation at a required timing such as a timing of a start to use each medical device or a timing of a check during the use.

Figure 8:
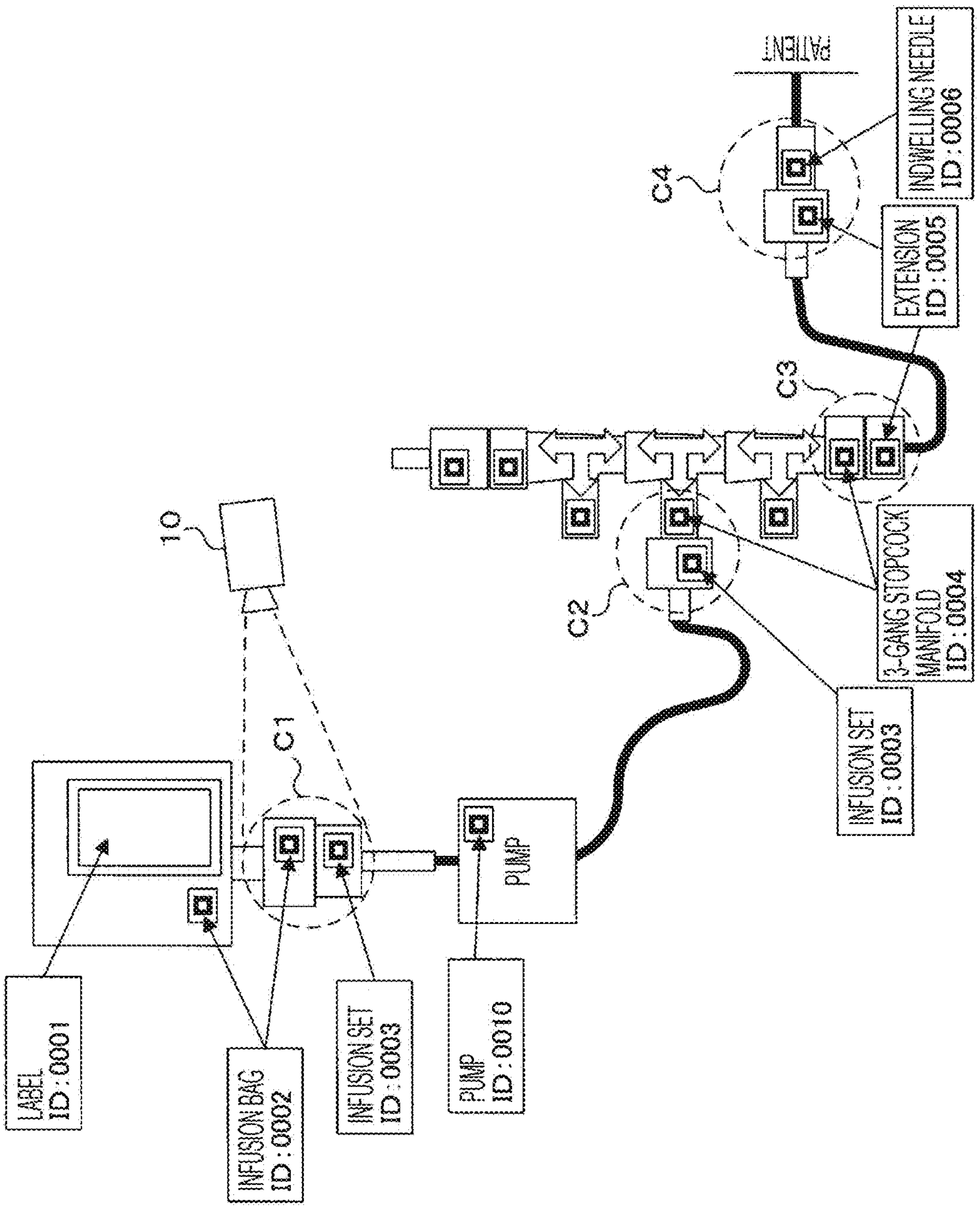
FIG. 8 is a diagram illustrating exemplary confirmation for management of the plurality of medical devices.

FIG. 8 is a diagram illustrating exemplary confirmation for management of a plurality of medical devices. The example illustrated in FIG. 8 is similar to that illustrated in FIG. 5. A medical worker captures an image of connection portions, using a smartphone, a tablet terminal, or a pair of AR goggles. FIG. 8 illustrates, as exemplary connection portions, connected connection portions C1 of "infusion bag: 0002" and "infusion set: 0003," connected connection portions C2 of "infusion set: 0003" and "3-gang stopcock manifold: 0004," connected connection portions C3 of "3-gang stopcock manifold: 0004" and "extension tube: 0005," and connected connection portions C4 of "extension tube: 0005" and "indwelling needle: 0006."

A medical worker may also capture an image of a predetermined operation on connection portions, using the input apparatus 10 such as a smartphone, a tablet terminal, or a pair of AR goggles. The predetermined operation includes additional tightening of the connection portions, and the like. A medical worker may visually inspect the connection portions, using a pair of AR goggles. The input apparatus 10 outputs, to the information processing apparatus 50, image data on a captured image of the connection portions, image data on a captured image of the operation of additionally tightening the connection portions, and image data on a captured image of the operation of visually inspecting the connection portions. Based on the acquired image data, the control unit 51 is capable of recording, in the storage unit 56 and the management apparatus 100, history information such as a connection state between the connection portions, a date and time of a determination on the connection state, a predetermined operation on the connection portions, a date and time of the predetermined operation, visual inspection of the connection portions, and a date and time of the visual inspection.

FIG. 9 is a diagram illustrating exemplary history information. The history information is a record of a connection confirmation, an additional tightening confirmation, a visual inspection confirmation, and the like as well as dates and times of these confirmations for each pair of the connected connection portions of the medical devices. With regard to, for example, the connected connection portions C1, a connection confirmation, a visual inspection confirmation, an additional tightening confirmation, a connection confirmation, carried out in sequence are recorded together with dates and times of these confirmations in chronological order. The same applies to the remaining connection portions.

As described above, the control unit 51 may record a date and time of a determination that the medical devices (the plurality of medical devices) are connected. It is thus possible to record a date and time of a start of the use of a medical device. It is therefore possible to utilize this date and time for a reference date and time of a confirmation and check of the medical device.

The control unit 51 may also determine whether a predetermined operation (e.g., additional tightening, visual inspection, etc.) is performed on connection portions by a medical worker, and record a date and time of the determination that the predetermined operation is performed. It is thus possible to, in takeover (transfer) at the time of work shifts of medical workers, allow the successor to easily recognize the operation history by the predecessor.

In addition, when determining that the predetermined operation is performed and then determining that the medical devices are connected, the control unit 51 may record a date and time of the determination. It is thus possible to confirm the effectiveness of the predetermined operation (e.g., additional tightening, visual inspection, etc.).

Figure 10:
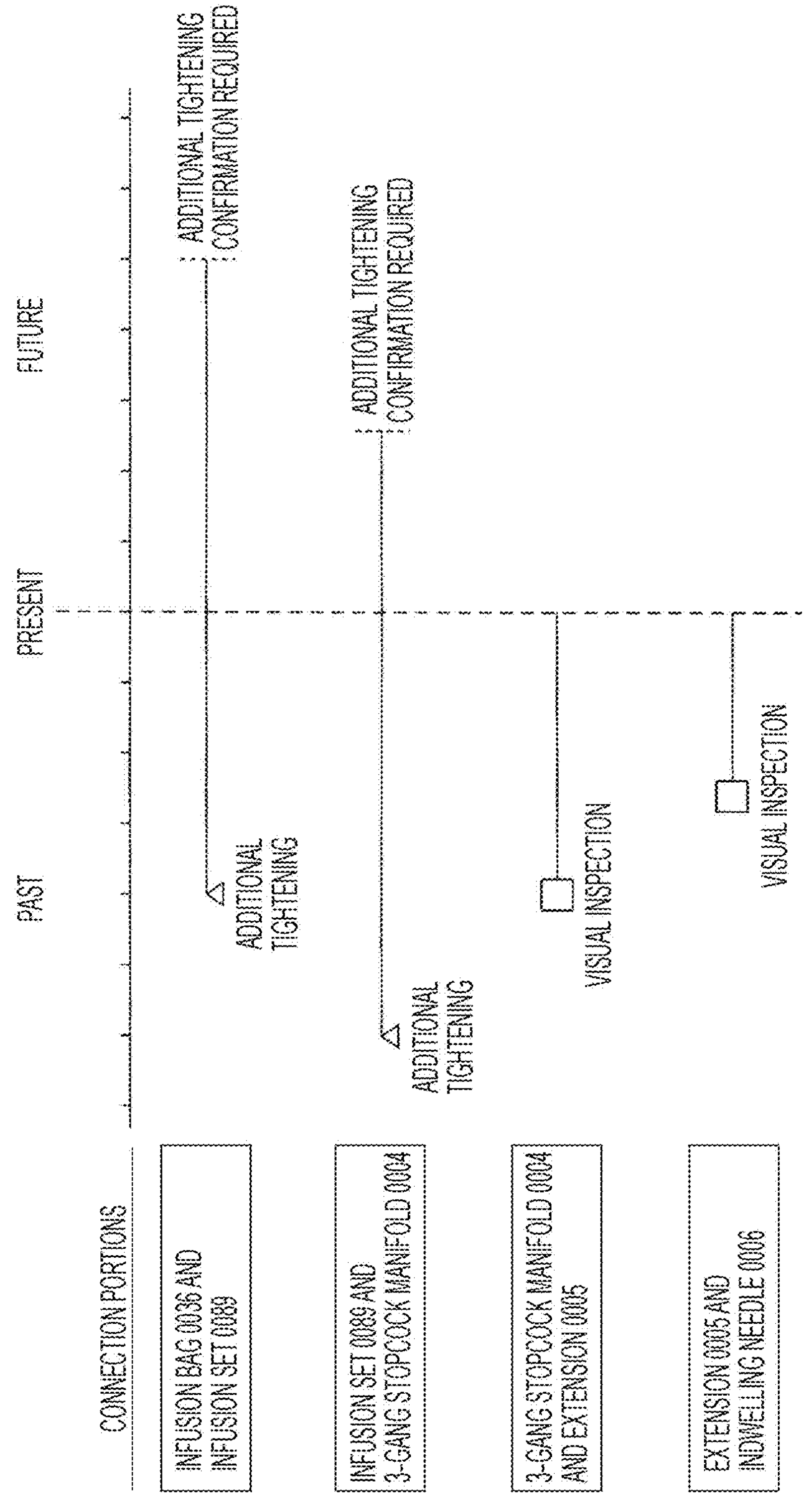
FIG. 10 is a diagram illustrating exemplary information provision in takeover.

FIG. 10 is a diagram illustrating exemplary support information in takeover. The support information can be displayed on the output apparatus 20, that is, a display panel of a smartphone or a tablet terminal, a monitor of a personal computer or the like, a pair of AR glasses of a pair of AR goggles, or the like. FIG. 10 illustrates the connection portions of the plurality of medical devices of which the predecessor takes charge. FIG. 10 illustrates, as the connection portions, the connected connection portions of "infusion bag: 0036" and "infusion set: 0089," the connected connection portions of "infusion set: 0089" and "3-gang stopcock manifold: 0004," the connected connection portions of "3-gang stopcock manifold: 0004" and "extension tube: 0005," and the connected connection portions of "extension tube: 0005" and "indwelling needle: 0006."

According to the support information, a horizontal axis corresponds to a past-to-future time axis with respect to a present date and time, and indicates what operation was performed on each pair of the connection portions and what time the operation was performed. In the example illustrated FIG. 10, a triangular mark indicates "additional tightening" and a square mark indicates "visual inspection." It is thus possible to allow the successor to recognize at a glance what operation was performed on each pair of the connection portions and what time the operation was performed. It is therefore possible to reduce workloads and mistakes of medical workers. It is also possible to easily manage the medical devices.

In addition, with regard to an operation to be performed periodically, such as additional tightening of connection portions, as illustrated in FIG. 10, a timing of additionally tightening connection portions of interest is displayed on the time axis together with a message such as "ADDITIONAL TIGHTENING CONFIRMATION REQUIRED" so that a medical worker recognizes the next timing of additional tightening which is calculated from the latest date and time of additional tightening. This facilitates management of the medical devices.

Figure 11A:
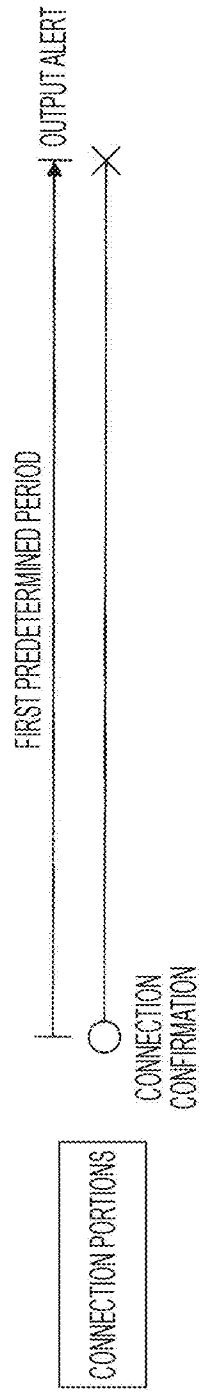
FIG. 11A is a diagram illustrating exemplary output of an attention attracting alert.

FIGS. 11A, 11B, 11C, and 11D are diagrams each illustrating exemplary output of an attention attracting alert. As illustrated in FIG. 11A, the control unit 51 may output an alert (warning) when a first predetermined period elapses from a date and time of a determination that the connection portions of the medical devices are connected. The alert may be output by displaying characters or may be output by voice. In addition, different sound effects may be used in accordance with the emergency of an alert. Examples of the first predetermined period may include 48 hours, 1 week, and the like. The first predetermined period can be set as appropriate in accordance with the type of a medical device. It is thus possible to suppress, for example, an excess of the expiration date of a medical device.

Figure 11B:
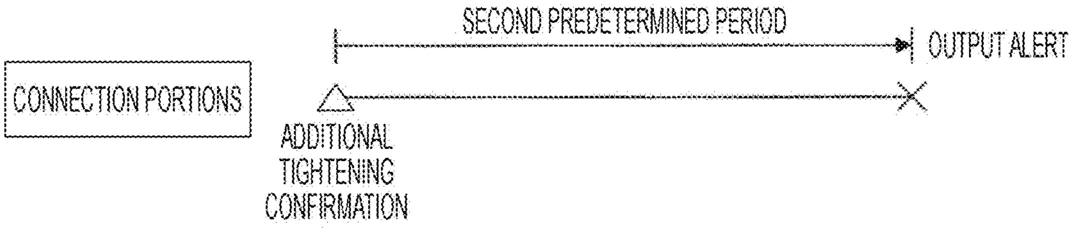
FIG. 11B is a diagram illustrating exemplary output of an attention attracting alert.

As illustrated in FIG. 11B, the control unit 51 may also output an alert when determining that the predetermined operation (e.g., additional tightening) is not performed on the connection portions within a second predetermined period from a date and time of the determination that the predetermined operation is performed on the connection portions. Examples of the second predetermined period may include 3 hours, 6 hours, 24 hours, and the like. The second predetermined period can be set as appropriate in accordance with the type of a medical device. It is thus possible to previously prevent disconnection of connection portions.

Figure 11C:
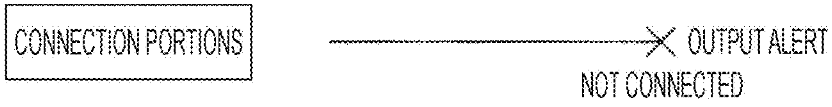
FIG. 11C is a diagram illustrating exemplary output of an attention attracting alert.

As illustrated in FIG. 11C, the control unit 51 may also output an alert (warning) when determining that the connection portions of the medical devices are not connected. It is thus possible to promptly address, for example, a situation in which a newly connected medical device is connected incompletely and a situation in which a connection portion connected once is disconnected due to a certain reason.

Figure 11D:
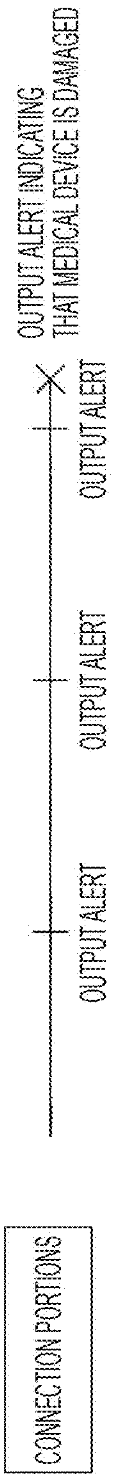
FIG. 11D is a diagram illustrating exemplary output of an attention attracting alert.

As illustrated in FIG. 11D, the control unit 51 may also output, when repeatedly outputting an alert for a specific one of the connection portions, an alert indicating that the corresponding medical device is damaged. It is considered that a connection portion is disconnected frequently because of damage to a connector or the like. It is therefore possible to immediately prompt a medical worker to replace the connection portion with a non-defective one.

Although not illustrated, the control unit 51 may output an alert when positions of the two-dimensional barcodes affixed to the respective connection portions change or when a frequency of change in the positions is a predetermined threshold value or more. It is thus possible to previously detect, for example, transition from a state in which the connection portions are normally connected to a state in which the connection portions are completely disconnected, and to take a required measure. Although not illustrated, the control unit 51 may also output, when determining that an internal pressure of a pump is continuously high, an alert indicating that a flow path is possibly closed.

Figure 12:
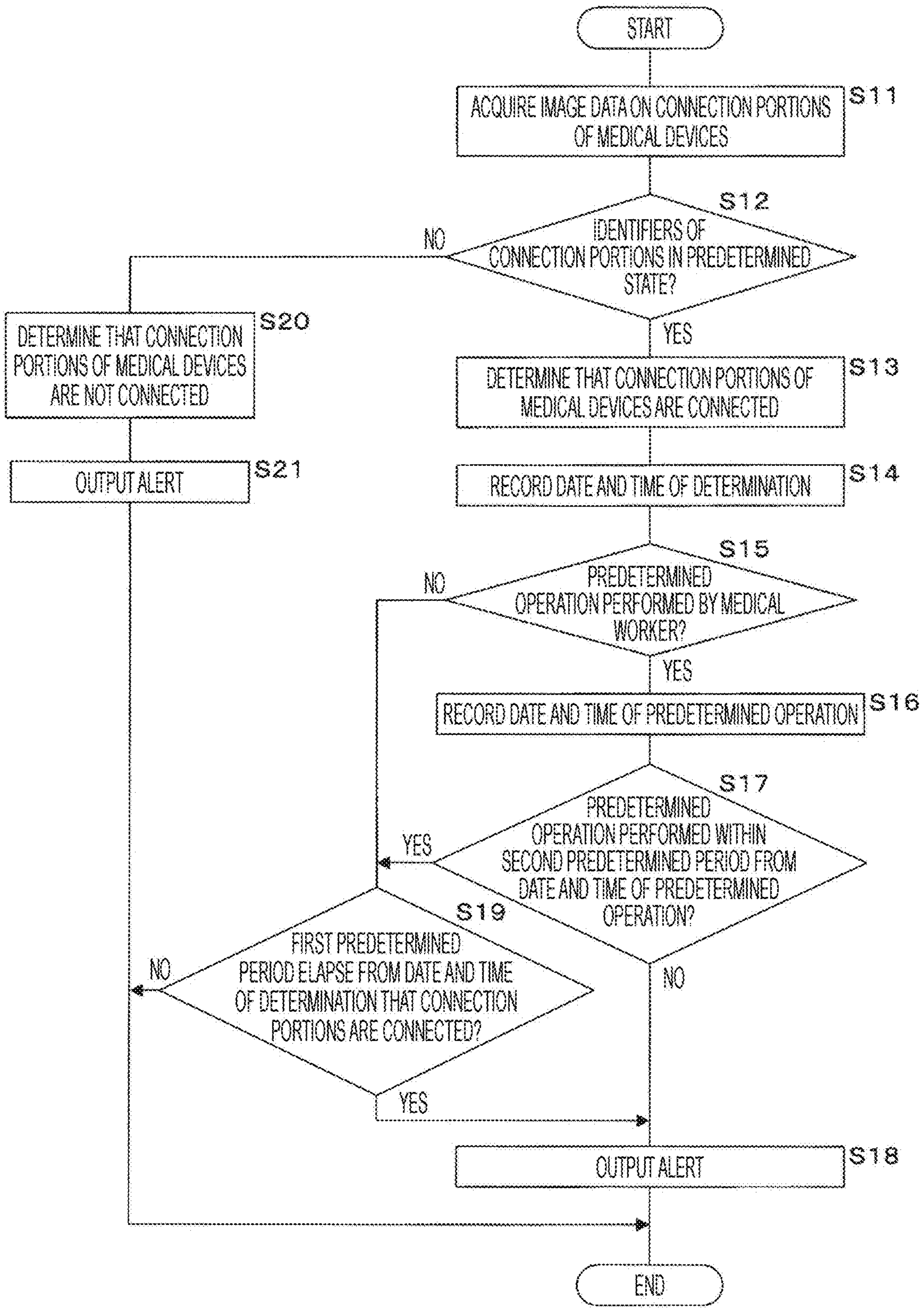
FIG. 12 is a diagram illustrating an exemplary procedure of the processing by the information processing apparatus.

FIG. 12 is a diagram illustrating an exemplary procedure of the processing by the information processing apparatus 50. For convenience, the following description will be given on the assumption that the control unit 51 mainly performs the processing. The control unit 51 acquires image data on the connection portions of the plurality of medical devices (S11), and determines whether the identifiers (e.g., barcodes, etc.) of the respective connection portions are in the predetermined state (S12). When the identifiers are in the predetermined state (YES in S12), the control unit 51 determines that the connection portions of the plurality of medical devices are connected (S13), and records a date and time of the determination (S14).

The control unit 51 determines whether the predetermined operation (e.g., additional tightening, visual inspection, etc.) is performed by the medical worker (S15). When the predetermined operation is performed (YES in S15), the control unit 51 records a date and time of the predetermined operation (S16). The control unit 51 determines whether the predetermined operation is performed within the second predetermined period from the date and time of the predetermined operation (S17).

When the predetermined operation is not performed within the second predetermined period (NO in S17), the control unit 51 outputs an alert (S18), and then ends the processing. When the predetermined operation is performed within the second predetermined period (YES in S17), the control unit 51 determines whether the first predetermined period elapses from the date and time of the determination that the connection portions are connected (S19). Examples of the first predetermined period may include 48 hours, 1 week, and the like. The first predetermined period can be set as appropriate in accordance with the type of a medical device. When the predetermined operation is not performed by the medical worker (NO in S15), the control unit 51 makes a determination in step S19.

When the first predetermined period elapses (YES in S19), the control unit 51 outputs an alert in step S18. When the first predetermined period does not elapse (NO in S19), the control unit 51 ends the processing. When the identifiers are not in the predetermined state (NO in S12), the control unit 51 determines that the connection portions of the plurality of medical devices are not connected (S20), outputs an alert (S21), and then ends the processing.

According to the present embodiment, as described above, it is possible to easily manage and observe a medical device and to provide work assistance to a medical worker; therefore, it is possible to reduce workloads and human mistakes.

REFERENCE NUMERAL LIST

1 Communication network
10 Input apparatus
20 Output apparatus
50 Information processing apparatus
51 Control unit
52 Communication unit
53 Interface unit
54 Image processing unit
55 Memory
56 Storage unit
60 Computer program
100 Management apparatus
110 Electronic medical record

The invention claimed is:

1. A connection state determination method for determining a connection state between a plurality of medical devices each including a connection portion having a unique identifier, the connection state determination method comprising:

detecting the connection portions of the respective medical devices;

determining whether the identifiers of the detected connection portions are in a predetermined state, wherein the predetermined state includes at least one of a state in which a separation distance between the identifiers of the respective connection portions is a predetermined distance or less and a state in which an arrangement of the identifiers of the respective connection portions is within a predetermined range;

determining the connection state between the plurality of medical devices based on whether the identifiers are in the predetermined state; and determining that the plurality of medical devices are connected in a case in which the identifiers are in the predetermined state.

2. The connection state determination method according to claim 1, comprising:

recording a date and time of a determination that the plurality of medical devices are connected.

3. The connection state determination method according to claim 1, comprising:

determining whether a predetermined operation is performed on the connection portions by a medical worker; and recording a date and time of a determination that the predetermined operation is performed.

4. The connection state determination method according to claim 3, comprising:

recording, in a case of determining that the predetermined operation is performed and then determining that the plurality of medical devices are connected, a date and time of a determination that the plurality of medical devices are connected.

5. The connection state determination method according to claim 1, comprising:

outputting a warning in a case of determining that the plurality of medical devices are not connected or in a case in which a first predetermined period elapses from a date and time of a determination that the plurality of medical devices are connected.

6. The connection state determination method according to claim 1, comprising:

outputting a warning in a case in which positions of the identifiers of the respective connection portions change or in a case in which a frequency of change in the positions is a predetermined threshold value or more.

7. The connection state determination method according to claim 1, comprising:

outputting a warning in a case of determining that a predetermined operation is not performed on the connection portions within a second predetermined period from a date and time of a determination that the predetermined operation is performed on the connection portions.

8. The connection state determination method according to claim 1, wherein:

the identifiers each comprise a barcode.

9. The connection state determination method according to claim 1, comprising:

detecting the connection portions of the respective medical devices by capturing an image of the connection portions with an input apparatus; and determining whether the identifiers of the detected connection portions are in the predetermined state, based on the captured image.

10. A connection state determination system for determining a connection state between a plurality of medical devices each including a connection portion having a unique identifier, the connection state determination system comprising:

a detection unit configured to detect the connection portions of the respective medical devices;

a control unit configured to:

determine whether the identifiers of the detected connection portions are in a predetermined state, wherein the predetermined state includes at least one of a state in which a separation distance between the identifiers of the respective connection portions is a predetermined distance or less and a state in which an arrangement of the identifiers of the respective connection portions is within a predetermined range, determine the connection state between the plurality of medical devices based on whether the identifiers are in the predetermined state, and determine that the plurality of medical devices are connected in a case in which the identifiers are in the predetermined state.

11. A connection state determination system for determining a connection state between a plurality of medical devices each including a connector having an identifier, the connection state determination system comprising:

an input apparatus configured to capture an image of the connectors of the medical devices, the input apparatus comprising a pair of augmented reality (AR) goggles, a smartphone, a tablet terminal, or a camera; and a control unit configured to determine, based on the captured image, whether the identifiers of the detected connectors are in a predetermined state, and determine the connection state between the plurality of medical devices based on whether the identifiers are in the predetermined state.

12. The connection state determination system according to claim 11, wherein:

the identifiers each comprise a barcode.

* * * * *